US010220198B2

(12) United States Patent
Fuchs et al.

(10) Patent No.: US 10,220,198 B2
(45) Date of Patent: Mar. 5, 2019

(54) CONNECTION DEVICE FOR A MEDICAL FLUID CONDUIT SYSTEM

(71) Applicant: B. Braun Melsungen AG, Melsungen (DE)

(72) Inventors: Jürgen Fuchs, Bad Emstal (DE); Jürgen Hartung, Hessisch Lichtenau (DE)

(73) Assignee: B. Braun Melsungen AG, Melsungen (DE)

(*) Notice: Subject to any disclaimer, the term of this patent is extended or adjusted under 35 U.S.C. 154(b) by 0 days.

(21) Appl. No.: 15/543,845

(22) PCT Filed: Jan. 14, 2016

(86) PCT No.: PCT/EP2016/050635
§ 371 (c)(1),
(2) Date: Jul. 14, 2017

(87) PCT Pub. No.: WO2016/113337
PCT Pub. Date: Jul. 21, 2016

(65) Prior Publication Data
US 2018/0001074 A1 Jan. 4, 2018

(30) Foreign Application Priority Data
Jan. 16, 2015 (DE) .................. 10 2015 200 613

(51) Int. Cl.
*A61M 39/10* (2006.01)
*A61M 39/12* (2006.01)
(Continued)

(52) U.S. Cl.
CPC ............ *A61M 39/12* (2013.01); *A61M 39/10* (2013.01); *A61M 39/1011* (2013.01); *A61M 39/223* (2013.01); *F16L 37/24* (2013.01)

(58) Field of Classification Search
CPC .. A61M 39/12; A61M 39/10; A61M 39/1011; A61M 2039/1027;
(Continued)

(56) References Cited

U.S. PATENT DOCUMENTS 5,423,776 A 6/1995 Haindl
6,641,177 B1 11/2003 Pinciaro
(Continued)

FOREIGN PATENT DOCUMENTS

DE 570905 C 2/1933
DE 4129781 A1 3/1993
(Continued)

OTHER PUBLICATIONS

International Search Report and Written Opinion for International Application No. PCT/EP2016/050635, dated Mar. 21, 2016—9 Pages.
(Continued)

*Primary Examiner* — Emily L Schmidt
*Assistant Examiner* — Nicholas J Chidiac
(74) *Attorney, Agent, or Firm* — RatnerPrestia

(57) ABSTRACT

A connection device includes a connection body which has a hose adapter and a connector piece for releasably fastening a further fluid conduit component or fluid storage component. The connection body is coaxially surrounded by a securing sleeve. The securing sleeve is axially securable on the connection body in two securing positions that are axially mutually spaced apart relative to a central longitudinal axis of the connection body. Rotatability of the securing sleeve is possible in a first securing position, and jamming of the securing sleeve on a hose portion that is plug-fitted onto the hose adapter is possible in a second securing position.

12 Claims, 4 Drawing Sheets

(51) Int. Cl.
   *A61M 39/22*  (2006.01)
   *F16L 37/24*  (2006.01)
(58) Field of Classification Search
   CPC .. A61M 2039/1044; A61M 2039/1066; A61M 2039/1033; F16L 37/24
   USPC .............................................. 285/23, 82, 86
   See application file for complete search history.

(56) References Cited

U.S. PATENT DOCUMENTS

| | | |
|---|---|---|
| 8,647,300 B2 | 2/2014 | Künzler et al. |
| 2016/0003391 A1 | 1/2016 | Okita et al. |

FOREIGN PATENT DOCUMENTS

| | | |
|---|---|---|
| DE | 29709252 U1 | 8/1997 |
| DE | 20109061 U1 | 8/2001 |
| DE | 10321309 A1 | 1/2004 |
| DE | 102008008332 A1 | 8/2009 |
| DE | 102015108596 A1 | 1/2016 |
| WO | 2009055949 A1 | 5/2009 |
| WO | 2010028052 A1 | 3/2010 |
| WO | 2010088512 A1 | 8/2010 |

OTHER PUBLICATIONS

German Search Report for German Application No. 10 2015 200 613.1, dated Jul. 31, 2015—9 Pages.

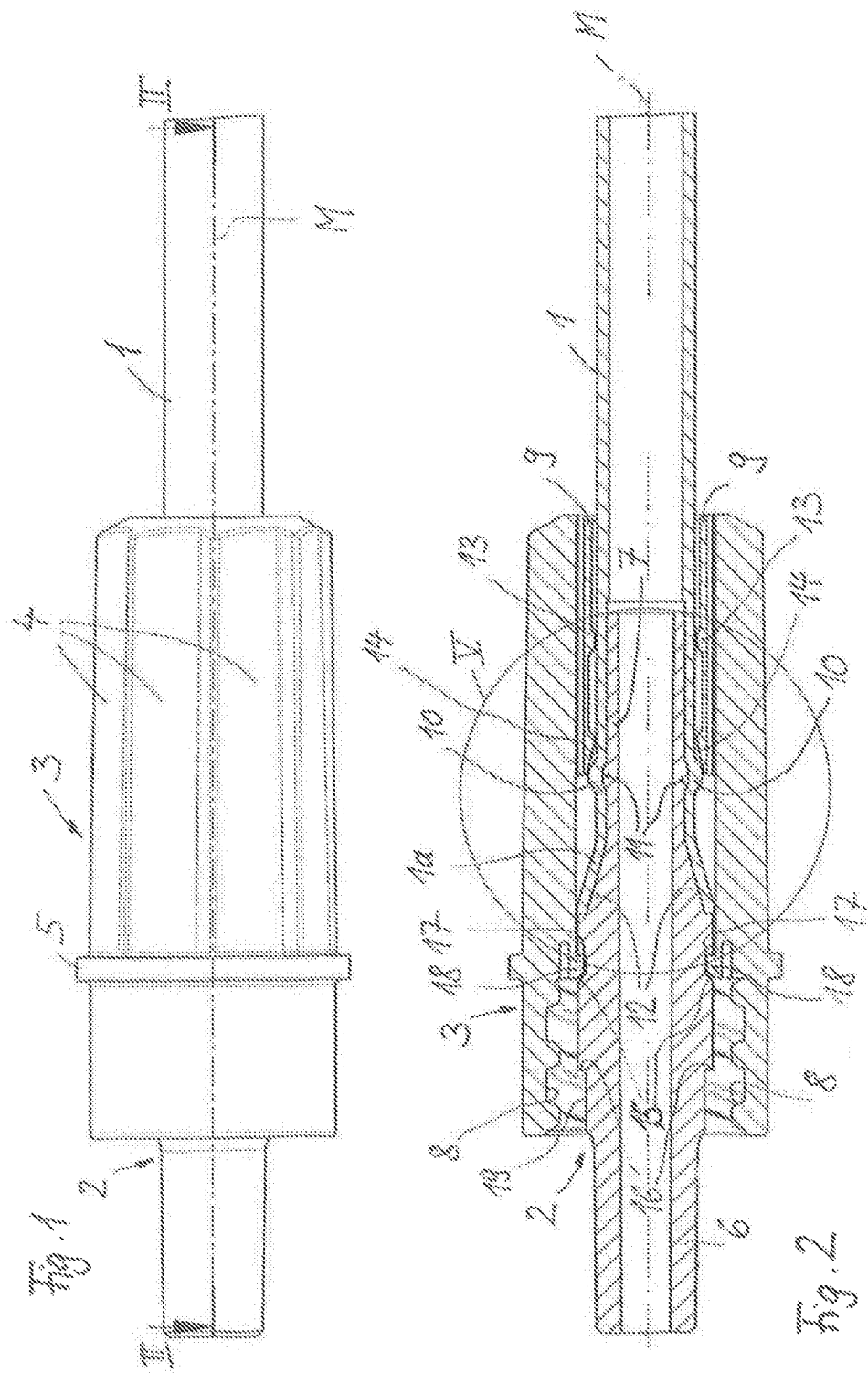

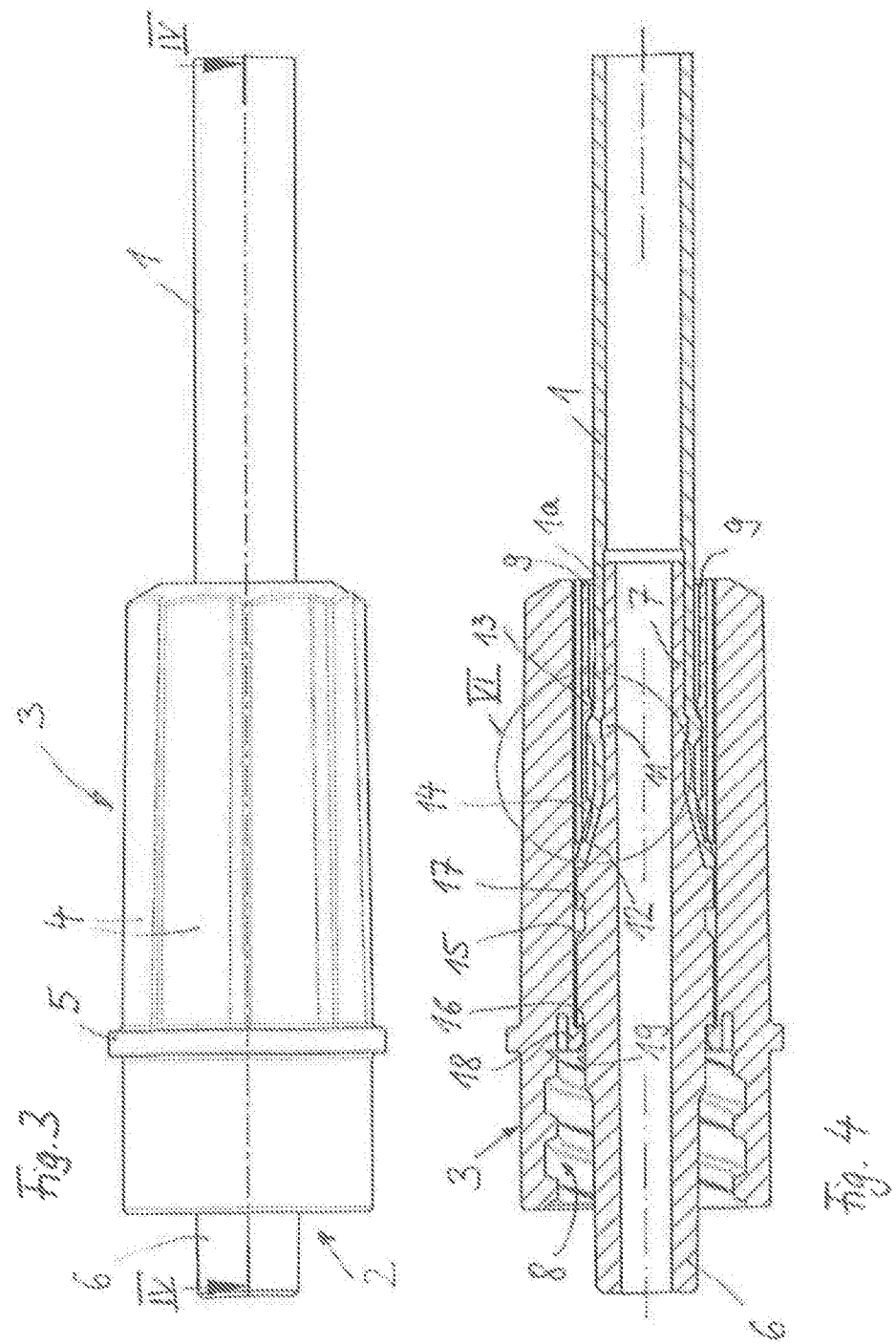

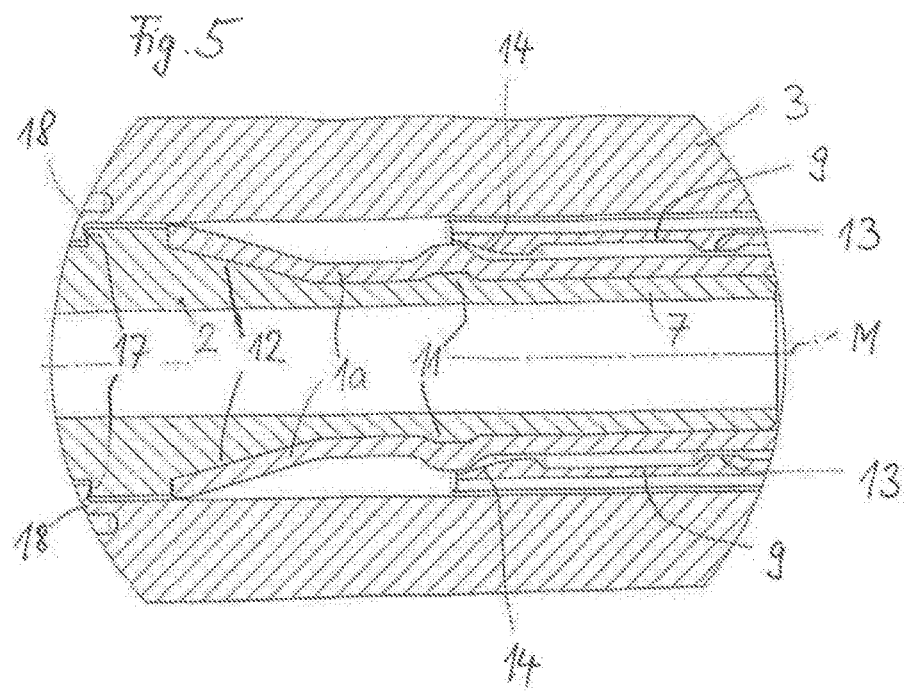
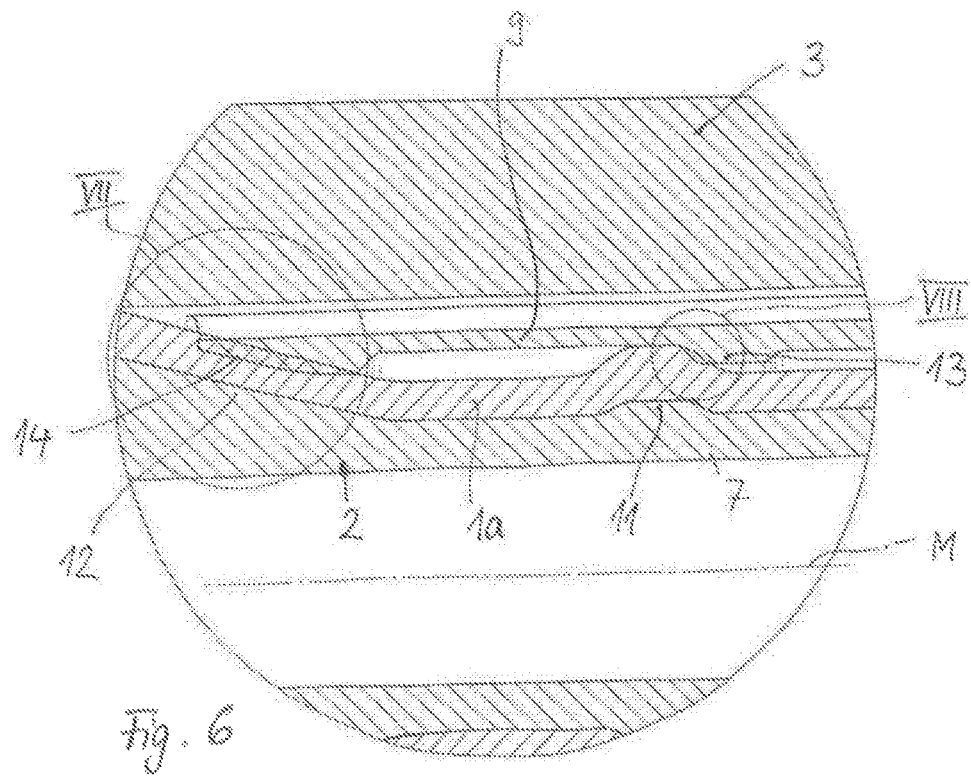

CONNECTION DEVICE FOR A MEDICAL FLUID CONDUIT SYSTEM

RELATED APPLICATIONS

This is the United States National Phase of International Application No. PCT/EP2016/050635, filed Jan. 14, 2016, which is related to and claims the benefit of priority of German Application No. DE 10 2015 200 613.1, filed Jan. 16, 2015. The contents of International Application No. PCT/EP2016/050635 and German Application No. DE 10 2015 200 613.1 are incorporated by reference herein in their entireties.

FIELD

The invention relates generally to a connection device for a medical fluid conduit system, and more particularly to a connection device having a connection body which has a hose adapter and a connector piece for releasably fastening a further fluid conduit component or storage component, wherein the connection body is coaxially surrounded by a securing sleeve, and wherein in an operationally ready state a hose conduit is connected to the hose adapter. The invention moreover relates to a medical fluid conduit system having a hose conduit and a connection device for fastening a further fluid conduit component or fluid storage component, wherein the connection device has a connection body to which a hose portion of the hose conduit is connected.

BACKGROUND

Medical fluid conduit systems usually have a hose conduit, the hose portion on the end side of which is adhesively bonded to a hose adapter of a connection body. The connection body on the front end region thereof that is opposite the hose adapter has a connector piece for fastening a further fluid conduit component or fluid storage component. The connection body is surrounded by a securing sleeve which is provided with a female Luer lock thread so as to allow connection to a male Luer lock thread of the respective fluid conduit component or fluid storage component which is to be connected. On account of the hose portion being adhesively bonded to the connection body, both the hose material of the hose portion as well as the material of the connection body must have suitable physical and chemical properties in order for a stable adhesive connection to be guaranteed in conjunction with a respective adhesive.

It is desirable to achieve a connection device and a medical fluid conduit system of the type mentioned at the outset which guarantee simple handling and an improved application potential.

SUMMARY is the aforementioned desire can be achieved in terms of the connection device in that a hose portion is plug-fitted in an adhesive-free manner onto the hose adapter, and in that the securing sleeve is axially securable on the connection body in two securing positions that are axially mutually spaced apart relative to a central longitudinal axis of the connection body, wherein rotatability of the securing sleeve relative to the hose portion is provided in a first securing position, and jamming of the securing sleeve on the hose portion that is plug-fitted onto the hose adapter is provided in a second securing position.

A connection between a hose conduit and the connection body is achieved by the solution according to the invention by clamping a respective hose portion on the hose adapter of the connection body. Adhesive bonding of the hose portion to a respective hose adapter of a connection body is avoided on account thereof. By virtue of jamming the hose portion in a merely mechanical manner in relation to the connection body and to the securing sleeve, the selection of material pairings is no longer dependent on suitable adhesive materials and adhesive methods being adapted to. Aging issues of the adhesive, which in the case of the prior art could lead to adhesive bonding and sealing issues, are avoided by the solution according to the invention. Material pairings which would not be compatible in the case of adhesive bonding, in particular polypropylene and a thermoplastic elastomer (TPE), can be selected for the hose conduit and for the connection body and/or the securing sleeve on account of the solution according to the invention. Depending on the embodiment, the connection body can be embodied so as to be integral or in multiple parts. In one preferred embodiment, a check valve is integrated in the connection body. The connection body is part of a connection device which can be employed within a medical fluid conduit system. The connection body can be provided as part of a drip chamber. Alternatively, the connection body is part of a medical infusion or transfusion system. Advantageously, the connection device is part of a single-use conduit system for medical infusion applications, the former, once used, being disposed of. Advantageously, the connection body is embodied as a connector on which the securing sleeve is held. Advantageously, jamming and consequently sealing of the hose portion on the hose adapter of the connection body is performed in a common motion conjointly with connecting the securing sleeve to a further fluid conduit component or fluid storage component, in particular to a catheter, a syringe, or a further connector. The securing sleeve is preferably embodied as a loose Luer lock nut such that a connection to a complementary Luer lock component forcibly also causes jamming, sealing, and securing of the hose portion on the connection body. The transition of the securing sleeve from the first to the second securing position, and on account thereof the respective sealing and clamping of the hose portion in a radial and axial manner between the securing sleeve and the hose adapter, is performed when the Luer lock nut, i.e. the sealing sleeve, is being tightened. By contrast, rotatability of the securing sleeve relative to the connection body, even in the case of a hose portion that has already been plug-fitted, is provided in the first securing position. When the securing sleeve is being tightened from the first securing position, on account of which the securing sleeve apart from a rotating movement also performs an axial movement in the direction of the second securing position, there is consequently no action of force nor a transmission of torque to an external jacket of the hose portion, such that any torsioning of the hose portion is avoided.

In a design embodiment of the invention, the connection body and the securing sleeve have mutually complementary profiled latching features which define the first and the second securing position of the securing sleeve on the connection body, wherein at least one profiled latching feature at least in portions is embodied so as to be resilient in a radially elastic manner in order for an audible latching of the profiled latching feature to be enabled in the first and/or the second securing position. The complementary profiled latching features guarantee a reliable, clearly defined, and axially secured positioning of the securing sleeve relative to the connection body. Rotatability of the securing sleeve is still guaranteed in the first securing position, despite axial securing by means of the profiled latching features. The audible latching of the at least one profiled latching feature improves the handling of the connection device by medical nursing staff. Audible latching is advantageously provided only when the at least one profiled latching feature has reached the second securing position of the securing sleeve on the connection body, said second securing position simultaneously guaranteeing sealing and clamping of the hose portion on the connection body. The medical nursing staff is provided an acoustic signal that a sealed and clamped securing position of the securing sleeve has been reached by way of the audible latching in the second securing position.

In a further design embodiment of the invention, the connection body in the region of the hose adapter is provided with a run-up ramp region that when viewed in the plug-fitting direction of a hose portion is disposed on the end side. On account thereof, the hose portion when being plug-fitted is elastically widened at the front end side, on account of which improved clamping of the hose portion on the hose adapter results. The run-up ramp region can be formed by one encircling run-up ramp portion or by a plurality of run-up ramp portions that are disposed so as to be distributed across the circumference of the hose adapter.

In a further design embodiment of the invention, the run-up ramp region is designed as a conically widening surface area. The conically widening surface area forms an encircling oblique run-up face which necessarily correspondingly widens a front end region of the hose portion when the hose portion is being plug-fitted, on account of which an improved clamping effect of the hose portion in this run-up ramp region is achieved.

In a further design embodiment of the invention, the securing sleeve on an end region that is assigned to the connector piece of the connection body is provided with profiled Luer lock connectors. The securing sleeve in this end region is preferably embodied as a Luer lock nut, such that the securing sleeve is provided with female profiled Luer lock connectors. The securing sleeve in the first securing position up to the axial displacement to the second securing position as well as in the second securing position is disposed so as to be rotatable relative to the connection body. However, rotatability of the securing sleeve relative to the jammed hose portion is no longer provided in the second securing position, such that continued rotation of the securing sleeve in the second securing position relative to the connection body is preferably performed only by way of limited rotation angles which at least largely avoids warping of the hose conduit that comprises the hose portion.

In a further design embodiment of the invention, the securing sleeve on another end region that is assigned to the hose adapter has a clamping sleeve portion which in relation to the central longitudinal axis of the connection body is disposed so as to be at least partially radially elastically resilient and in the second securing position of the securing sleeve exerts a radial and/or axial clamping effect on the hose portion. The clamping sleeve portion is advantageously molded so as to be integral to the securing sleeve. The radial elastic resilience of the clamping sleeve portion enables an interaction with an external circumference of the hose adapter of the connection body when being clamped, and a deformation of the hose portion.

In a further design embodiment of the invention, the clamping sleeve portion is formed by a plurality of clamping lugs that are disposed so as to be uniformly distributed across an internal circumference of the securing sleeve. The clamping lugs are integrally connected to the securing sleeve and in the production of the clamping sleeve are achieved by a respective design of the mold of a plastics injection molding tool.

In a further design embodiment of the invention, the clamping sleeve portion and the hose adapter have mutually complementary profiled clamping features which in the first and/or the second securing position exert a radial and/or axial clamping effect on the hose portion. The profiled clamping features are preferably provided so as to be integral on an external circumference of the hose adapter, or on an internal circumference of the clamping sleeve portion, respectively, and have the effect of deforming the hose portion on the external and internal side as soon as the first or the second securing position of the securing sleeve has been reached, to the extent that the hose portion is plug-fitted onto the hose adapter.

In a further design embodiment of the invention, the clamping sleeve portion when viewed in the plug-fitting direction of the hose portion is provided on a forward front end region with a support ramp region which for clamping the hose portion at the end side interacts with the run-up ramp region of the hose adapter of the connection body. The mutually complementary oblique run-up planes of the support ramp region and of the run-up ramp region in the case of an axial movement of the securing sleeve necessarily have the effect of a clamping and deforming effect of the hose portion that increases as the axial movement continues.

In a further design embodiment of the invention, the mutually complementary profiled latching features of the securing sleeve and of the connection body for the second securing position are designed in such a manner that the securing sleeve in the plug-fitting direction of the hose portion is axially movable in a limited manner relative to the connection body, and that the securing sleeve in the opposite axial direction is axially blocked. On account thereof, the securing sleeve, even when the latter has reached the second securing position, by corresponding torsioning can be pulled axially even farther in the direction of the assigned connection component, in particular of the fluid conduit component or fluid storage component, over the Luer lock thread, on account of which a further increase in the sealing and clamping effect on the hose portion results. However, releasing the securing sleeve from the second securing position in the opposite direction is not possible.

In a further design embodiment of the invention, the profiled latching features of the securing sleeve are designed as a plurality of latching cams that are disposed so as to be distributed across an internal circumference of the securing sleeve, said latching cams being disposed on the securing sleeve so as to be elastically resilient in a radial and limited manner. The latching cams are molded so as to be integral to the securing sleeve and are preferably provided on web appendices which protrude so as to be axially parallel with a central longitudinal axis of the securing sleeve, guaranteeing a radial and elastic resilience of the latching cams.

In a further design embodiment of the invention, the securing sleeve in the region of an external jacket is provided with profiled grip features for manually handling the securing sleeve. On account thereof, simple torsioning of the securing sleeve that is readily detectable in a sensory manner is guaranteed.

In terms of the medical fluid conduit system of the type mentioned at the outset, the object underlying the invention is achieved in that the connection device is embodied according to at least one of the afore-described embodiments or design embodiments. The medical fluid conduit system is preferably provided as a hose conduit system of a medical infusion system.

BRIEF DESCRIPTION OF THE DRAWING FIGURES

Further advantages and features of the invention are derived from the description hereunder of a preferred exemplary embodiment of the invention which is illustrated by means of the drawings in which:

FIG. 1 shows an embodiment of a connection device according to the invention for a medical fluid conduit system in a side view.

FIG. 2 shows the connection device as per FIG. 1 in a sectional illustration along the section line II-II in FIG. 1.

FIG. 3 shows the connection device as per FIG. 1 in a second securing position of a securing sleeve, said second securing position being axially offset in relation to the illustration in FIG. 1.

FIG. 4 shows the connection device as per FIG. 3 in a longitudinal section along the section line IV-IV in FIG. 3.

FIG. 5 shows a fragment V of the connection device as per FIG. 2 in an enlarged illustration.

FIG. 6 shows a fragment VI of the connection device according to FIG. 4 in an enlarged illustration.

DETAILED DESCRIPTION

Figure 7:
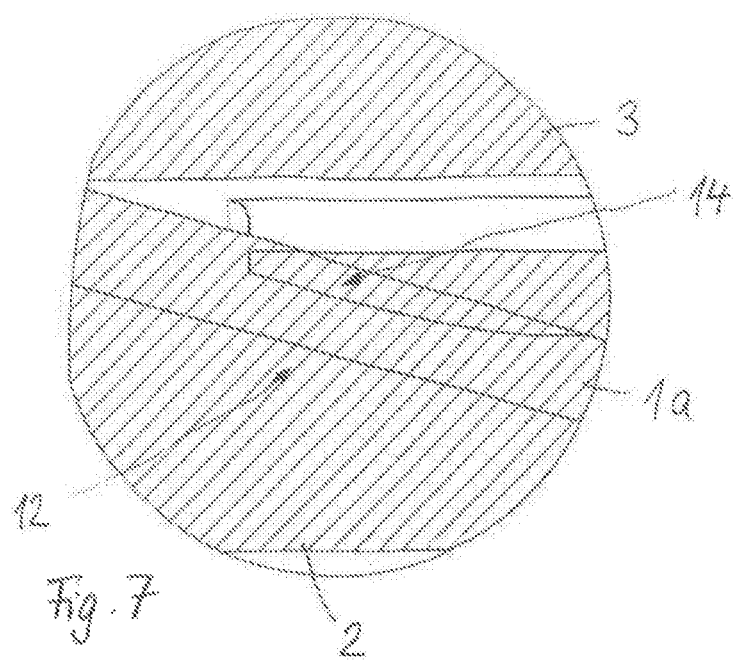
FIG. 7 shows a fragment VII of FIG. 6 in a more enlarged illustration.
Figure 8:
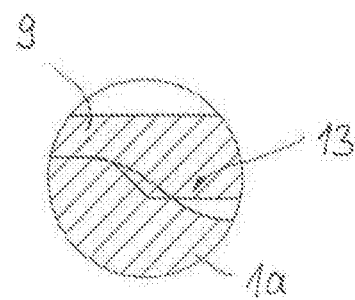
FIG. 8 shows a fragment VIII of FIG. 6 in an enlarged illustration.

A connection device as per FIGS. 1 to 8 is part of a medical fluid conduit system in the form of an infusion system. The connection device serves for connecting a hose conduit 1 to a medical fluid conduit or fluid storage component of the medical fluid conduit system. The hose conduit 1 has an end-side hose portion 1a which in relation to the hose conduit 1 has a reduced wall thickness and therefore increased flexibility. The hose conduit 1 including the hose portion 1a is made of an elastically flexible plastics material, presently from a thermoplastic elastomer, preferably silicone.

The connection device moreover has an integral connection body 2 made of a thermoplastic plastics material, presently of polypropylene. The connection body 2 in relation to a central longitudinal axis M of the connection body is surrounded by an annular securing sleeve 3. The securing sleeve 3 represents a plastics part that is separate from the connection body 2 and from the hose conduit 1 and is likewise embodied so as to be integral.

The connection body 2 in the case of the exemplary embodiment illustrated has a cylindrical passage duct that extends so as to be coaxial with the central longitudinal axis M and is open toward opposite front end regions of the connection body 2. In the case of one exemplary embodiment (not illustrated) of the invention, a check valve is additionally integrated in the connection body 2. The connection body (not illustrated) is formed by two interconnected connection components that enclose the check valve therebetween.

The connection body 2 on a side that faces the hose conduit 1 has a hose adapter 7 onto which the hose portion 1a in the assembly of the hose conduit 1 is axially push-fitted. The connection body 2 in the region of the opposite side thereof is provided with a connector piece 6 which is embodied as a plug tip that slightly tapers in a conical manner toward a front end region.

The securing sleeve 3 on the external circumference thereof is provided with profiled grip features 4 for simple manual handling of the securing sleeve 3, on the one hand. On the other hand, the securing sleeve 3 on the external circumference thereof has an annular bead 5 which protrudes in a radially outward manner and axially delimits the profiled grip features 4. The annular bead 5 likewise serves for the simple manual handling of the securing sleeve 3.

The securing sleeve 3 on that side thereof that faces the connector piece 6 is provided with a female Luer lock thread which serves as a profiled Luer lock connector 8. The portion of the securing sleeve 3 thus formed consequently forms a Luer lock nut. The securing sleeve 3 on the internal circumference thereof and toward an opposite front end has an annular clamping sleeve portion 9 which is formed by a plurality of clamping lugs that run so as to be mutually parallel and are disposed so as to be uniformly distributed across the internal circumference of the securing sleeve 3. The clamping lugs extend along the internal circumference of the securing sleeve 3 so as to be parallel with the central longitudinal axis M. The clamping lugs 9 in the circumferential direction are integrally connected to the securing sleeve 3. However, a longitudinal gap which guarantees the radially elastic resilience of the respective clamping lug and thus of the clamping sleeve portion 9 is located radially outward, between the internal circumference of the securing sleeve 3 and the respective clamping lug. The securing sleeve 3 is likewise made of a thermoplastic plastics material, preferably from the same material as the connection body 2. The clamping sleeve portion 9 has an internal diameter which is larger than an external diameter of the hose conduit 1. The clamping sleeve portion 9 is provided with profiled clamping features 13, 14 which are axially mutually spaced apart and protrude in a knob-type and radially inward manner toward the hose portion 1a, or toward the hose conduit 1, respectively. An internal diameter of the clamping sleeve portion 9 in the region of these profiled clamping features 13 is slightly larger than or of equal size to an external diameter of the hose conduit 1 and of the hose portion 1a such that the securing sleeve 3 on the hose conduit 1 and on the hose portion 1a can be axially displaced or torsioned in the circumferential direction in a substantially free manner without any deformation of, and consequently any resistance by, the hose conduit 1 or the hose portion 1a arising.

The profiled clamping features 14 of the clamping sleeve portion 9 which are provided on a front end region of the clamping sleeve portion 9 that faces the profiled Luer lock connector 8 in each case have one run-up ramp that widens toward a front end.

The connection body 2 in the region of the hose adapter 7 has a profiled clamping feature 11 that is molded so as to be complementary on an external jacket, protrudes radially outward, and is embodied as a hump-shaped annular web. In a manner so as to be spaced apart from the profiled clamping feature 11 axially in the direction of the connector piece 6, the connection body 2 on an external circumference of the hose adapter 7 moreover has a run-up ramp region in the form of a conically widening surface area 12 which proceeding from a cylindrical external circumference of the hose adapter 7 widens in the direction of the connector piece 6. In a manner so as to axially adjoin the conically widening surface area 12, a cylindrical external surface area region of the connection body 2 is provided, the latter being provided with an annular groove shaped profiled latching feature 15, 17. The profiled latching feature 15, 17 has a latching shoulder 17 that is designed in a step-like manner and a friction shoulder 15 that extends toward the connector piece 6, runs in a conically oblique manner, and continues into the cylindrical external surface area of the connection body 2. A further profiled latching feature 16 which is designed as a radial annular shoulder is provided so as to be spaced apart axially in the direction of the connector piece 6, said profiled latching feature 16 transitioning into a cylindrical external surface area region 19 having an external diameter that is reduced in relation to the external surface area. The conically tapered plug tip which forms the connector piece 6 of the connection body 2 extends from the cylindrical external surface area region 19.

The securing sleeve 3 on the internal circumference thereof, in a manner so as to axially adjoin the profiled Luer lock connector 8, is provided with elastically resilient profiled latching features 18 which are molded so as to be integral to the securing sleeve 3 and are formed by a plurality of latching cams 18 that are disposed so as to be distributed across the internal circumference of the securing sleeve 3. The latching cams 18 protrude in a radially inward manner and are disposed on webs that are elastically resilient in a radial manner.

The profiled clamping features 14 form a support ramp region which is embodied so as to be complementary to the run-up ramp region 12 of the connection body 2 and has the effect of axially and radially clamping the hose portion 1a on the hose adapter 7 of the connection body 2.

In order for the connection device and the respective medical fluid conduit system to be assembled, the securing sleeve 3 in a first step is push-fitted from an end side axially onto the hose conduit 1. The hose conduit 1 by way of the hose portion 1a is subsequently plug-fitted axially onto the hose adaptor 7 of the connection body 2, preferably by sliding or push-fitting the hose portion 1a. The hose portion 1a is push-fitted onto the hose adaptor 7 so far until a front end region of the hose portion 1a slides along the run-up ramp region 12 and is widened, and until an end periphery of the hose portion 1a comes to bear on an annular shoulder (not referred to in more detail) that delimits the run-up ramp region 12.

The securing sleeve 3 is subsequently displaced axially from the hose conduit 1 in the direction of the connection body 2 until the latching cams 18 audibly latch into the annular groove shaped profiled latching feature 15, 17. In this position the first securing position of the securing sleeve 3 relative to the connection body 2 has been reached. The securing sleeve 3 by virtue of the mounting of the latching cams 18 in the annular groove shaped profiled latching feature 15, 17 is axially secured on the connection body 2, on the one hand, and is mounted so as to be rotatable relative to the connection body 2, on the other hand. The clamping sleeve portion is partially push-fitted axially onto the hose portion 1a. The support ramp region of the profiled clamping feature 14 of the clamping sleeve portion 9 in the first securing position of the securing sleeve 3, which can be seen by means of FIG. 2, bears on a bulging hose region 10 of the hose portion 1a and has the effect of axially and radially clamping the hose portion 1a to some extent, in addition to the clamping to which the hose portion 1a by virtue of the elastic widening thereof has already been inherently subjected on the external circumference of the hose adapter 7.

This first securing position of the securing sleeve 3 corresponds to a standby position of the connection device prior to the latter being connected to another connector of a fluid conduit component or fluid storage component in a medical application. As soon as the connection device in the first securing position according to FIG. 2 is now offered up to a complementary connection component of the medical fluid system, in particular of the medical infusion system, the connector piece 6 and the profiled Luer lock connectors 8 of the connection device in a manner not illustrated in more detail come into contact with complementary profiled Luer lock connectors and with a plug receptacle of the connection component. The complementary profiled Luer lock connectors of the connection component not illustrated are embodied as male profiled Luer lock connectors, so as to be able to establish a connection between the connection component and the securing sleeve 3. As soon as the plug receptacle of the connection component and the plug tip of the connector piece 6 of the connection body 2 have been plugged into one another so far that axial pre-fixing has been achieved, the securing sleeve 3 is torsioned, on account of which the Luer lock nut of the securing sleeve 3 is forcibly tightened on the male profiled Luer lock connectors of the connection component. Since the connection body 2 per se is already axially blocked by the connection component, the securing sleeve 3 in addition to the rotating movement thereof forcibly slides axially along the external surface area region of the connection body 2, wherein the latching cams 18 slide out of the profiled latching feature 15, 17 along the run-up shoulder 15. As soon as the latching cams 18 have been displaced axially beyond the profiled latching feature 16, the latching cams 18 again audibly latch into the profiled latching feature 16 that is formed by the radial annular shoulder. The second securing position according to FIG. 4 has then been reached.

Conjointly with the axial displacement of the securing sleeve 3, the clamping sleeve portion 9 in the transition from the first securing position to the second securing position has also been forcibly displaced axially along the hose adapter 7, on account of which the support ramp portion of the profiled clamping feature 14 runs up on the front end region of the hose portion 1a that has been widened on the run-up ramp region 12 and, on account thereof, is elastically deformed in an outward manner. Additionally, the profiled clamping feature 13 runs up on the hump-type bulging 10 of the hose portion 1a in the region of the profiled clamping feature 11 that is provided on the external circumference of the hose adapter 7, and here causes an additional deformation and additional radial and axial clamping of the hose portion 1a. The positioning of the support ramp region of the profiled clamping feature 14 and of the profiled clamping feature 13 relative to the hose portion 1a and relative to the connection body 2 in this second securing position of the securing sleeve 3 is illustrated in an enlarged manner by means of FIGS. 7 and 8.

Since the radial annular shoulder portion of the connection body 2 that forms the profiled latching feature 16 for the second securing position is adjoined by the cylindrical external surface area 19 having a diameter that is reduced in relation to the external surface area of the connection body, the securing sleeve 3 also in this second securing position can still be displaced farther axially in the direction of the front end of the plug tip, that is to say of the connector piece 6. Reaching the second securing position is in any case likewise identifiable by an operator when handling the securing sleeve 3 by way of an audible latching. If the securing sleeve 3 by way of the profiled Luer lock connectors 8 is rotated even farther in the direction of closure, the securing sleeve 3 can still move farther axially in the direction of the connector piece 6, on account of which the clamping effect of the support ramp region 14 and of the profiled clamping features 13 on the hose portion 1*a* is further increased.

Releasing the securing sleeve 3 from the connection body 2 once the second securing position has been reached is not readily possible, in particular not without damaging the securing sleeve 3. This is also not necessary, since the connection device and the respective hose conduit system are embodied as disposable instruments for single use.

The invention claimed is:

1. A connection device for a medical fluid conduit system, the connection device having a connection body which has a hose adapter and a connector piece for releasably fastening a further fluid conduit component or fluid storage component, the connection body being coaxially surrounded by a securing sleeve, and wherein in an operationally ready state a hose conduit is connected to the hose adapter, a hose portion of the hose conduit being plug-fitted in an adhesive-free manner onto the hose adapter, and the securing sleeve being axially securable on the connection body in two securing positions that are axially mutually spaced apart relative to a central longitudinal axis of the connection body, wherein rotatability of the securing sleeve relative to the hose portion is provided in a first securing position, and jamming of the securing sleeve on the hose portion that is plug-fitted onto the hose adapter is provided in a second securing position, wherein the connection body and the securing sleeve have mutually complementary profiled latching features which define the first and the second securing position of the securing sleeve on the connection body, wherein at least one profiled latching feature at least in portions is embodied so as to be resilient in a radially elastic manner in order for an audible latching of the profiled latching feature to be enabled in the first and/or the second securing position.

2. The connection device according to claim 1, wherein the connection body in a region of the hose adapter is provided with a run-up ramp region that when viewed in a plug-fitting direction of a hose portion is disposed on an end side.

3. The connection device according to claim 2, wherein the run-up ramp region is designed as a conically widening surface area.

4. The connection device according to claim 1, wherein the securing sleeve on an end region that is assigned to the connector piece of the connection body is provided with profiled Luer lock connectors.

5. The connection device according to claim 1, wherein the securing sleeve on an end region that is assigned to the hose adapter has a clamping sleeve portion, which in relation to the central longitudinal axis of the connection body, is disposed so as to be at least partially radially elastically resilient, the clamping sleeve portion exerting a radial and/or axial clamping effect on the hose portion when the securing sleeve is in the second securing position.

6. The connection device according to claim 5, wherein the clamping sleeve portion is formed by a plurality of clamping lugs that are disposed so as to be uniformly distributed across an internal circumference of the securing sleeve.

7. The connection device according to claim 5, wherein the clamping sleeve portion and the hose adapter have mutually complementary profiled clamping features which in the first and/or the second securing position exert a radial and/or axial clamping effect on the hose portion.

8. The connection device according to claim 7, wherein the clamping sleeve portion when viewed in the plug-fitting direction of the hose portion is provided on a forward front end region with a support ramp region which for clamping the hose portion at the end side interacts with the run-up ramp region of the hose adapter of the connection body.

9. The connection device according to claim 1, wherein the mutually complementary profiled latching features of the securing sleeve and of the connection body for the second securing position are designed in such a manner that the securing sleeve in the plug-fitting direction of the hose portion is axially movable in a limited manner relative to the connection body, and that the securing sleeve in the opposite axial direction is axially blocked.

10. The connection device according to claim 1, wherein the profiled latching features of the securing sleeve are designed as a plurality of latching cams that are disposed so as to be distributed across an internal circumference of the securing sleeve, said latching cams being disposed on the securing sleeve so as to be elastically resilient in a radial and limited manner.

11. The connection device according to claim 1, wherein the securing sleeve in the region of an external jacket is provided with profiled grip features for manually handling the securing sleeve.

12. A medical fluid conduit system having a hose conduit and a connection device for fastening a further fluid conduit component or fluid storage component, wherein the connection device has a connection body to which a hose portion of the hose conduit is connected, wherein the connection device comprises the connection device of claim 1.

* * * * *